US011286225B2

(12) United States Patent
Veliath et al.

(10) Patent No.: US 11,286,225 B2
(45) Date of Patent: Mar. 29, 2022

(54) ORGANOLEPTIC COMPOUNDS

(71) Applicant: International Flavors & Fragrances Inc., New York, NY (US)

(72) Inventors: Elizabeth D. Veliath, Union Beach, NJ (US); Richard K. Payne, Union Beach, NJ (US); Anubhav P. S. Narula, Union Beach, NJ (US); Paul D. Jones, Union Beach, NJ (US); Gary J. Mertz, Union Beach, NJ (US); Michael G. Monteleone, Union Beach, NJ (US)

(73) Assignee: International Flavors & Fragrances Inc., Union Beach, NJ (US)

( * ) Notice: Subject to any disclaimer, the term of this patent is extended or adjusted under 35 U.S.C. 154(b) by 0 days.

(21) Appl. No.: 17/268,739

(22) PCT Filed: Aug. 15, 2019

(86) PCT No.: PCT/US2019/046601
§ 371 (c)(1),
(2) Date: Feb. 16, 2021

(87) PCT Pub. No.: WO2020/037098
PCT Pub. Date: Feb. 20, 2020

(65) Prior Publication Data
US 2021/0179521 A1    Jun. 17, 2021

Related U.S. Application Data

(60) Provisional application No. 62/765,037, filed on Aug. 17, 2018.

(51) Int. Cl.
*C07C 43/196* (2006.01)
*A61Q 13/00* (2006.01)

(52) U.S. Cl.
CPC ............ *C07C 43/196* (2013.01); *A61Q 13/00* (2013.01); *C07C 2603/78* (2017.05)

(58) Field of Classification Search
CPC .............................. C07C 43/196; A61Q 13/00
See application file for complete search history.

(56) References Cited

FOREIGN PATENT DOCUMENTS

| JP | 2003137758 A | 5/2003 |
| WO | 2017070131 A2 | 4/2017 |

OTHER PUBLICATIONS

Bhatia et al. (2008) "Fragrance material review on beta-caryophyllene alcohol," Food and Chemical Toxicology 46: S95-S96.
Collado et al. (1996) "The cleavage of caryophyllene oxide catalysed by tetracyanoethylene," Tetrahedron 52 (23):7961-7972.
International Search Report and Written Opinion in PCT/US2019/046601 dated Dec. 6, 2019.

*Primary Examiner* — Arrie L Reuther

(57) ABSTRACT

The present invention relates to novel ((4,4,8-trimethyltricyclo[6.3.1.0$^{2,5}$]dodecan-1-yl)oxy) alcohols and their use as fragrance materials.

20 Claims, No Drawings

ORGANOLEPTIC COMPOUNDS

This application is a U.S. National Stage Application of PCT/US2019/046601 filed Aug. 15, 2019 and claims priority to U.S. Provisional Patent Application Ser. No. 62/765,037, filed Aug. 17, 2018, the contents of each of which are incorporated by reference in their entirety.

STATUS OF RELATED APPLICATION

This application claims priority to U.S. Provisional Patent Application No. 62/765,037, filed Aug. 17, 2018, the contents hereby incorporated by reference as if set forth in its entirety.

FIELD OF THE INVENTION

The present invention relates to new chemical entities and the incorporation and use of the new chemical entities as fragrance materials.

BACKGROUND OF THE INVENTION

There is an ongoing need in the fragrance industry to provide new chemicals to give perfumers and other persons the ability to create new fragrances for perfumes, colognes and personal care products. Those with skill in the art appreciate how differences in the chemical structure of the molecule can result in significant differences in the odor, notes and characteristics of a molecule. These variations and the ongoing need to discover and use the new chemicals in the development of new fragrances allow the perfumers to apply the new compounds in creating new fragrances.

SUMMARY OF THE INVENTION

The present invention provides novel compounds and their unexpected advantageous use in enhancing, improving or modifying the fragrance of perfumes, colognes, toilet water, fabric care products, personal products and the like.

More specifically, the present invention relates to novel ((4,4,8-trimethyltricyclo[6.3.1.0$^{2,5}$]dodecan-1-yl)oxy) alcohols represented by Formula I set forth below:

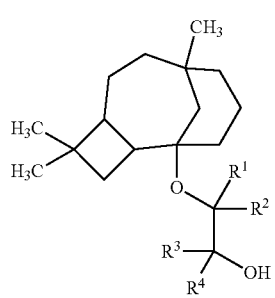

Formula I or an isomer thereof, wherein $R^1$, $R^2$, $R^3$ and $R^4$ are independently selected from the group consisting of hydrogen and a $C_{1-12}$ linear or branched alkyl group, with the proviso that $R^1$, $R^2$, $R^3$ and $R^4$ together contain 1-12 carbon atoms.

Another embodiment of the present invention relates to a subgenus of the above Formula I represented by Formula II set forth below:

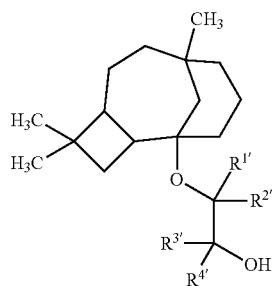

Formula II or an isomer thereof, wherein $R^{1'}$, $R^{2'}$, $R^{3'}$ and $R^{4'}$ are independently selected from the group consisting of hydrogen and a $C_{1-6}$ linear or branched alkyl group, with the proviso that $R^{1'}$, $R^{2'}$, $R^{3'}$ and $R^{4'}$ together contain 1-6 carbon atoms.

Another embodiment of the present invention relates to a novel compound selected from the group consisting of 2-((4,4,8-trimethyltricyclo[6.3.1.0$^{2,5}$]dodecan-1-yl)oxy)propan-1-ol;

1-((4,4,8-trimethyltricyclo[6.3.1.0$^{2,5}$]dodecan-1-yl)oxy)propan-2-ol;

2-((4,4,8-trimethyltricyclo[6.3.1.0$^{2,5}$]dodecan-1-yl)oxy)butan-1-ol;

1-((4,4,8-trimethyltricyclo[6.3.1.0$^{2,5}$]dodecan-1-yl)oxy)butan-2-ol;

2-((4,4,8-trimethyltricyclo[6.3.1.0$^{2,5}$]dodecan-1-yl)oxy)pentan-1-ol;

1-((4,4,8-trimethyltricyclo[6.3.1.0$^{2,5}$]dodecan-1-yl)oxy)pentan-2-ol;

2-((4,4,8-trimethyltricyclo[6.3.1.0$^{2,5}$]dodecan-1-yl)oxy)hexan-1-ol;

1-((4,4,8-trimethyltricyclo[6.3.1.0$^{2,5}$]dodecan-1-yl)oxy)hexan-2-ol;

3-((4,4,8-trimethyltricyclo[6.3.1.0$^{2,5}$]dodecan-1-yl)oxy)butan-2-ol;

an isomer thereof; and a mixture thereof.

Another embodiment of the present invention relates to a fragrance formulation comprising the novel compounds provided above.

Another embodiment of the present invention relates to a fragrance product comprising the novel compounds provided above.

Another embodiment of the present invention relates to a method of improving, enhancing or modifying a fragrance formulation through the addition of an olfactory acceptable amount of the novel compounds provided above.

These and other embodiments of the present invention will be apparent by reading the following specification.

DETAILED DESCRIPTION OF THE INVENTION

The ((4,4,8-trimethyltricyclo[16.3.1.0$^{2,5}$]dodecan-1-yl)oxy) alcohols represented by Formula I and Formula II of the present invention are illustrated, for example, by following examples.

2-((4,4,8-Trimethyltricyclo[6.3.1.0$^{2,5}$]dodecan-1-yl)
oxy)propan-1-ol (Structure 1)

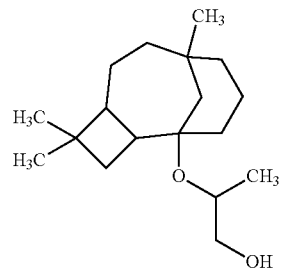 [SMILES: CC(CO)OC12CCCC(C)(CCC3C1CC3(C)C)C2]

1-((4,4,8-Trimethyltricyclo[6.3.1.0$^{2,5}$]dodecan-1-yl)
oxy)propan-2-ol (Structure 2)

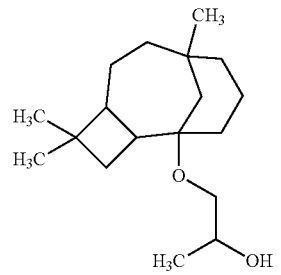 [SMILES: CC(O)COC12CCCC(C)(CCC3C1CC3(C)C)C2]

2-((4,4,8-Trimethyltricyclo[6.3.1.0$^{2,5}$]dodecan-1-yl)
oxy)butan-1-ol (Structure 3)

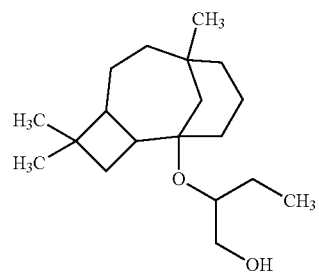 [SMILES: CCC(CO)OC12CCCC(C)(CCC3C1CC3(C)C)C2]

1-((4,4,8-Trimethyltricyclo[6.3.1.0$^{2,5}$]dodecan-1-yl)
oxy)butan-2-ol (Structure 4)

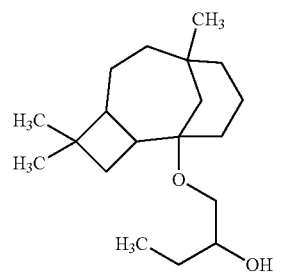

2-((4,4,8-Trimethyltricyclo[6.3.1.0$^{2,5}$]dodecan-1-yl)
oxy)pentan-1-ol (Structure 5)

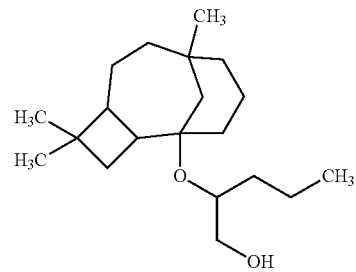 [SMILES: CCCC(CO)OC12CCCC(C)(CCC3C1CC3(C)C)C2]

1-((4,4,8-Trimethyltricyclo[6.3.1.0$^{2,5}$]dodecan-1-yl)
oxy)pentan-2-ol (Structure 6)

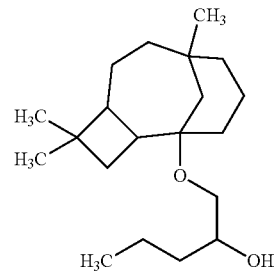 [SMILES: CCCC(O)COC12CCCC(C)(CCC3C1CC3(C)C)C2]

2-((4,4,8-Trimethyltricyclo[6.3.1.0$^{2,5}$]dodecan-1-yl)
oxy)hexan-1-ol (Structure 7)

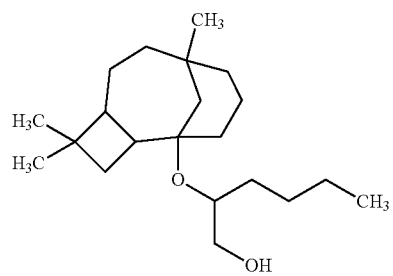 [SMILES: CCCCC(CO)OC12CCCC(C)(CCC3C1CC3(C)C)C2]

1-((4,4,8-Trimethyltricyclo[6.3.1.0$^{2,5}$]dodecan-1-yl)
oxy)hexan-2-ol (Structure 8)

3-((4,4,8-Trimethyltricyclo[6.3.1.0²,⁵]dodecan-1-yl)oxy)butan-2-ol (Structure 9)

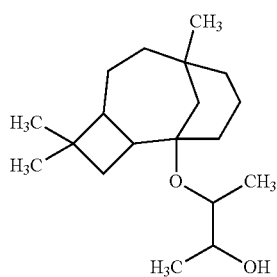 [SMILES: CC(O)C(C)OC12CCCC(C)(CCC3C1CC3(C)C)C2]

2-((4,4,8-Trimethyltricyclo[6.3.1.0²,⁵]dodecan-1-yl)oxy)pentan-3-ol (Structure 10)

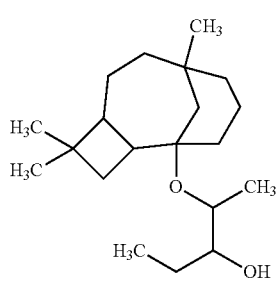 [SMILES: CCC(O)C(C)OC12CCCC(C)(CCC3C1CC3(C)C)C2]

3-((4,4,8-Trimethyltricyclo[6.3.1.0²,⁵]dodecan-1-yl)oxy)pentan-2-ol (Structure 11)

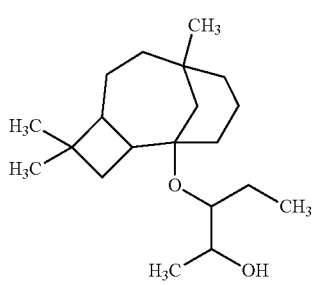 [SMILES: CCC(OC12CCCC(C)(CCC3C1CC3(C)C)C2)C(C)O]

2-Methyl-1-((4,4,8-trimethyltricyclo[6.3.1.0²,⁵]dodecan-1-yl)oxy)propan-2-ol (Structure 12)

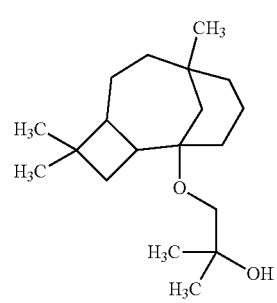 [SMILES: CC(C)(O)COC12CCCC(C)(CCC3C1CC3(C)C)C2]

The ((4,4,8-trimethyltricyclo[6.3.1.0²,⁵]dodecan-1-yl)oxy) alcohols of the present invention may be prepared via a general scheme depicted as follows:

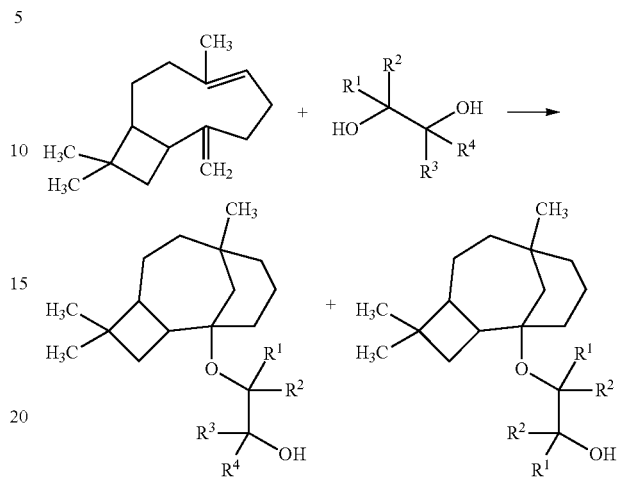

wherein $R^1$, $R^2$, $R^3$ and $R^4$ are defined as above.

Those with skill in the art will recognize that some of the compounds of the present invention contain chiral centers, thereby providing a number of stereoisomers of the claimed compounds. It is intended herein that the compounds of the present invention include isomeric mixtures as well as individual isomers that may be separated using techniques known to those having skill in the art. In certain embodiments, positional isomers such as (1,4,4-trimethyltricyclo[6.3.1.0²,⁵]dodecan-8-yl)oxy alcohols and (1,1,7-trimethyl-decahydro-3a,7-methanocyclopenta[8]annulen-3-yl)oxy alcohols are also included as the compounds of the present invention. Suitable techniques include chromatography such as high performance liquid chromatography, referred to as HPLC, particularly silica gel chromatography, and gas chromatography trapping known as GC trapping. Yet, commercial versions of such products are mostly offered as mixtures.

In these preparations, the compounds of the present invention can be used alone or in combination with other perfuming compositions, solvents, adjuvants and the like. The nature and variety of the other ingredients that can also be employed are known to those with skill in the art. Many types of fragrances can be employed in the present invention, the only limitation being the compatibility with the other components being employed. Suitable fragrances include but are not limited to fruits such as almond, apple, cherry, grape, pear, pineapple, orange, strawberry, raspberry; musk, flower scents such as lavender-like, rose-like, iris-like, carnation-like. Other pleasant scents include herbal and woodland scents derived from pine, spruce and other forest smells. Fragrances may also be derived from various oils, such as essential oils, or from plant materials such as peppermint, spearmint and the like.

A list of suitable fragrances is provided in U.S. Pat. No. 4,534,891, the contents of which are incorporated by reference as if set forth in its entirety. Another source of suitable fragrances is found in *Perfumes, Cosmetics and Soaps*, Second Edition, edited by W. A. Poucher, 1959. Among the fragrances provided in this treatise are acacia, cassis, chypre, cyclamen, fern, gardenia, hawthorn, heliotrope, honeysuckle, hyacinth, jasmine, lilac, lily, magnolia, mimosa, narcissus, freshly-cut hay, orange blossom, orchid, reseda, sweet pea, trefle, tuberose, vanilla, violet, wallflower, and the like.

The compounds of the present invention can be used in combination with a complementary fragrance compound. The term "complementary fragrance compound" as used herein is defined as a fragrance compound selected from the group consisting of 2-[(4-methylphenyl)methylene]-heptanal (Acalea), iso-amyl oxyacetic acid allylester (Allyl Amyl Glycolate), 4,4,10,10,11,12,12-heptamethyl-3-oxatricyclo[7.3.0.0<2,6>]dodecane (Amber Xtreme), (3,3-dimethylcyclohexyl)ethyl ethyl propane-1,3-dioate (Applelide), (E/Z)-1-ethoxy-1-decene (Arctical), 2-ethyl-4-(2,2,3-trimethyl-3-cyclo-penten-1-yl)-2-buten-1-ol (Bacdanol), 2-methyl-3-[(1,7,7-trimethylbicyclo[2.2.1]hept-2-yl)oxy]exo-1-propanol (Bornafix), 1,2,3,5,6,7-hexahydro-1,1,2,3,3-pentamethyl-4H-inden-4-one (Cashmeran), trimethylcyclopentenylmethyloxabicyclooctane (Cassiffix), 1,1-dimethoxy-3,7-dimethyl-2,6-octadiene (Citral DMA), 3,7-dimethyl-6-octen-1-ol (Citronellol), 3A,4,5,6,7,7A-hexahydro-4,7-methano-1H-inden-5/6-yl acetate (Cyclacet), 3A,4,5,6,7,7A-hexahydro-4,7-methano-1H-inden-5/6-yl propinoate (Cyclaprop), 3A,4,5,6,7,7A-hexahydro-4,7-methano-1G-inden-5/6-yl butyrate (Cyclobutanate), 1-(2,6,6-trimethyl-3-cyclohexen-1-yl)-2-buten-1-one (Delta Damascone), 3-(4-ethylphenyl)-2,2-dimethyl propanenitrile (Fleuranil), 3-(O/P-ethylphenyl) 2,2-dimethyl propionaldehyde (Floralozone), tetrahydro-4-methyl-2-(2-methylpropyl)-2H-pyran-4-ol (Floriffol), 1,3,4,6,7,8-hexahydro-4,6,6,7,8,8-hexamethylcyclopenta-gamma-2-benzopyran (Galaxolide), 1-(5,5-dimethyl-1-cyclohexen-1-yl)pent-4-en-1-one (Galbascone), E/Z-3,7-dimethyl-2,6-octadien-1-yl acetate (Geranyl Acetate), α-methyl-1,3-benzodioxole-5-propanal (Helional), 1-(2,6,6-trimethyl-2-cyclohexen-1-yl)-1,6-heptadien-3-one (Hexalon), (Z)-3-hexenyl-2-hydroxybenzoate (Hexenyl Salicylate, CIS-3), 4-(2,6,6-trimethyl-2-cyclohexen-1-yl)-3-buten-2-one (Ionone α), 1-(1,2,3,4,5,6,7,8-octahydro-2,3,8,8-tetramethyl-2-naphthalenyl)-ethan-1-one (Iso E Super), methyl 3-oxo-2-pentylcyclopentaneacetate (Kharismal), 2,2,4-trimethyl-4-phenyl-butanenitrile (Khusinil), 3,4,5,6,6-pentamethylhept-3-en-2-one (Koavone), 3/4-(4-hydroxy-4-methyl-pentyl) cyclohexene-1-carboxaldehyde (Lyral), 3-methyl-4-(2,6,6-trimethyl-2-cyclohexen-1-yl)-3-buten-2-one (Methyl Ionone γ), 1-(2,6,6-trimethyl-2-cyclohexen-1-yl) pent-1-en-3-one (Methyl Ionone α Extra, Methyl Ionone N), 3-methyl-4-phenylbutan-2-ol (Muguesia), cyclopentadec-4-en-1-one (Musk Z4), 3,3,4,5,5-pentamethyl-11,13-dioxatricyclo[7.4.0.0<2,6>]tridec-2(6)-ene (Nebulone), 3,7-dimethyl-2,6-octadien-1-yl acetate (Neryl Acetate), 3,7-dimethyl-1,3,6-octatriene (Ocimene), ortho-tolylethanol (Peomosa), 3-methyl-5-phenylpentanol (Phenoxanol), 1-methyl-4-(4-methyl-3-pentenyl) cyclohex-3-ene-1-carboxaldehyde (Precyclemone B), 4-methyl-8-methylene-2-adamantanol (Prismantol), 2-ethyl-4-(2,2,3-trimethyl-3-cyclopenten-1-yl)-2-buten-1-ol (Sanjinol), 2-methyl-4-(2,2,3-trimethyl-3-cyclopenten-1-yl)-2-buten-1-ol (Santaliff), 3-[cis-4-(2-methylpropyl)cyclohexyl]propanal (Starfleur), Terpineol, 2,4-dimethyl-3-cyclohexene-1-carboxaldehyde (Triplal), decahydro-2,6,6,7,8,8-hexamethyl-2H-indeno[4,5-B]furan (Trisamber), 2-tert-butylcyclohexyl acetate (Verdox), (3E)-4-methyldec-3-en-5-one (Veridian), 4-tert-butylcyclohexyL acetate (Vertenex), acetyl cedrene (Vertofix), 3,6/4,6-dimethylcyclohex-3-ene-1-carboxaldehyde (Vertoliff) and (3Z)-1-[(2-methyl-2-propenyl)oxy]-3-hexene (Vivaldie).

As used herein, the term "a" or "an" is understood to mean one or more. The term "a compound" is understood to mean one or more of the compounds represented by Formula I or Formula II as described herein. The preparation of the compounds of the present invention is detailed in the Examples. Materials were purchased from Aldrich Chemical Company unless noted otherwise.

The term "alkyl" means a linear or branched saturated monovalent hydrocarbon. Examples include, for example, but not limited to, methyl, ethyl, propyl, 2-propyl, butyl (including all isomeric forms), pentyl (including all isomeric forms), hexyl (including all isomeric forms), and the like. The term "alkenyl" means a linear or branched unsaturated, aliphatic hydrocarbon containing at least one carbon-carbon double bond. The term "alkylene" refers to bivalent alkyl. Examples include, for example, but not limited to, —$CH_2$—, —$CH_2CH_2$—, —$CH_2CH_2CH_2$—, —$CH_2(CH_3)CH_2$—, —$CH_2CH_2CH_2CH_2$—, and the like.

The term "cycloalkyl" means a saturated monocyclic, fused bicyclic, or fused tricyclic, monovalent hydrocarbon radical of three to fourteen carbon ring atoms. Unless otherwise stated, the valency of the group may be located on any atom of any ring within the radical, valency rules permitting. More specifically, examples include, for example, but not limited to, cyclopropyl, cyclobutyl, cyclopentyl, cyclohexyl, cycloheptyl, decahydronaphthyl (e.g., decahydronaphth-1-yl, decahydronaphth-2-yl, and the like), norbornyl, and the like. The cycloalkyl ring is unsubstituted or may be substituted with one or more ring system substituents which may be the same or different, and are as defined herein. The term "cycloalkenyl" means a one or more double bond-containing monocyclic, fused bicyclic, or fused tricyclic, monovalent hydrocarbon radical of three to fourteen carbon ring atoms. Unless otherwise stated, the valency of the group may be located on any atom of any ring within the radical, valency rules permitting. More specifically, examples include, for example, but not limited to, cyclopropenyl, cyclobutenyl, cyclopentenyl, cyclohexenyl, and the like. The cycloalkenyl ring is unsubstituted or may be substituted with one or more ring system substituents which may be the same or different, and are as defined herein.

The term "ring system substituent" means a substituent attached to an aromatic or non-aromatic ring system, which, for example, replaces an available hydrogen on the ring system. Ring system substituents may be the same or different, each being independently being, e.g., C(=NH)(NH$_2$), —NHC(=NH)(NH$_2$), alkyl, alkenyl, alkynyl, alkoxy, acyl, alkylcarbonylamino, carboxy, carboxyalkyl, alkoxycarbonyl, alkoxycarbonylalkyl, cyano, nitro, alkylthio, halo, haloalkyl, haloalkoxy, amino, alkylamino, dialkylamino, aminocarbonyl, alkyl aminocarbonyl, dialkylaminocarbonyl, alkyl sulfonyl, cycloalkylsulfonyl, alkylsulfonylamino, alkylaminosulfonyl, haloalkylamino, oxo, hydroxy, hydroxyalkyl, hydroxyalkyloxy, hydroxyalkyloxyalkyl, alkoxyalkyloxyalkyl, aryl, heteroaryl, cycloalkyl, cycloalkylamino, cycloalkyloxy, heteroaralkyloxy, aminoalkyl, aminoalkyloxy, alkoxyalkyl, alkoxyalkylcarbonyl, alkoxyalkyloxy, haloalkoxyalkyl, aryloxyalkyl, heteroaryloxyalkyl, heterocycloalkyl, heterocycloalkyloxyalkyl, heterocycloalkylalkyl, heterocycloalkylalkyloxy, or heterocycloalkyloxy. "Ring system substituent" may also mean a single moiety that simultaneously replaces two available hydrogens on two adjacent carbon atoms (one H on each carbon) on a ring system. Examples of such moieties are methylenedioxy and ethylenedioxy.

The terms "fragrance formulation", "fragrance composition", and "perfume composition" mean the same and refer to a consumer composition that is a mixture of compounds including, for example, alcohols, aldehydes, ketones, esters, ethers, lactones, nitriles, natural oils, synthetic oils, and mercaptans, which are admixed so that the combined odors of the individual components produce a pleasant or desired fragrance. The fragrance formulation of the present invention is a consumer composition comprising a compound of the present invention. The fragrance formulation of the present invention comprises a compound of the present invention and further a complementary fragrance compound as defined above.

The terms "fragrance product" and "functional product" mean the same and refer to a consumer product containing a fragrance ingredient that adds fragrance or masks malodor. Fragrance products may include, for example, perfumes, colognes, toilet water, bar soaps, liquid soaps, shower gels, foam baths, cosmetics, personal care and skin care products such as creams, lotions and shaving products, hair care products for shampooing, rinsing, conditioning, bleaching, coloring, dyeing and styling, deodorants and antiperspirants, feminine care products such as tampons and feminine napkins, baby care products such as diapers, bibs and wipes, family care products such as bath tissues, facial tissues, paper handkerchiefs or paper towels, fabric care products such as fabric softeners and fresheners, air care products such as air fresheners and fragrance delivery systems, cosmetic preparations, cleaning products and disinfectants such as detergents, dishwashing materials, scrubbing compositions, glass and metal cleaners such as window cleaners, countertop cleaners, floor and carpet cleaners, toilet cleaners and bleach additives, washing agents such as all-purpose, heavy duty, and hand washing or fine fabric washing agents including laundry detergents and rinse additives, dental and oral hygiene products such as toothpastes, tooth gels, dental flosses, denture cleansers, denture adhesives, dentifrices, tooth whitening and mouthwashes, health care and nutritional products and food products such as snack and beverage products. The fragrance product of the present invention is a consumer product that contains a compound of the present invention. The fragrance product of the present invention contains a compound of the present invention and further a complementary fragrance compound as defined above.

The term "improving" in the phrase "improving, enhancing or modifying a fragrance formulation" is understood to mean raising the fragrance formulation to a more desirable character. The term "enhancing" is understood to mean making the fragrance formulation greater in effectiveness or providing the fragrance formulation with an improved character. The term "modifying" is understood to mean providing the fragrance formulation with a change in character.

The term "olfactory acceptable amount" is understood to mean the amount of a compound in a fragrance formulation, wherein the compound will contribute its individual olfactory characteristics. However, the olfactory effect of the fragrance formulation will be the sum of effect of each of the fragrance ingredients. Thus, the compound of the present invention can be used to improve or enhance the aroma characteristics of the fragrance formulation, or by modifying the olfactory reaction contributed by other ingredients in the formulation. The olfactory acceptable amount may vary depending on many factors including other ingredients, their relative amounts and the olfactory effect that is desired.

The amount of the compounds of the present invention employed in a fragrance formulation varies from about 0.005 to about 70 weight percent, preferably from 0.005 to about 50 weight percent, more preferably from about 0.5 to about 25 weight percent, and even more preferably from about 1 to about 10 weight percent. Those with skill in the art will be able to employ the desired amount to provide desired fragrance effect and intensity. In addition to the compounds of the present invention, other materials can also be used in conjunction with the fragrance formulation to encapsulate and/or deliver the fragrance. Some well-known materials are, for example, but not limited to, polymers, oligomers, other non-polymers such as surfactants, emulsifiers, lipids including fats, waxes and phospholipids, organic oils, mineral oils, petrolatum, natural oils, perfume fixatives, fibers, starches, sugars and solid surface materials such as zeolite and silica. Some preferred polymers include polyacrylate, polyurea, polyurethane, polyacrylamide, polyester, polyether, polyamide, poly(acrylate-co-acrylamide), starch, silica, gelatin and gum Arabic, alginate, chitosan, polylactide, poly(melamine-formaldehyde), poly(urea-formaldehyde), or a combination thereof.

When used in a fragrance formulation these ingredients provide additional notes to make a fragrance formulation more desirable and noticeable, and add the perception of value. The odor qualities found in these materials assist in beautifying and enhancing the finished accord as well as improving the performance of the other materials in the fragrance.

In addition, the compounds of the present invention are also surprisingly found to provide superior ingredient performance and possess unexpected advantages in malodor counteracting applications such as body perspiration, environmental odor such as mold and mildew, bathroom, and etc. The compounds of the present invention substantially eliminate the perception of malodors and/or prevent the formation of such malodors, thus, can be utilized with a vast number of functional products.

Examples of the functional products are provided herein to illustrate the various aspects of the present invention. However, they do not intend to limit the scope of the present invention. The functional products may include, for example, a conventional room freshener (or deodorant) composition such as room freshener sprays, an aerosol or other spray, fragrance diffusers, a wick or other liquid system, or a solid, for instance candles or a wax base as in pomanders and plastics, powders as in sachets or dry sprays or gels, as in solid gel sticks, clothes deodorants as applied by washing machine applications such as in detergents, powders, liquids, whiteners or fabric softeners, fabric refreshers, linen sprays, closet blocks, closet aerosol sprays, or clothes storage areas or in dry cleaning to overcome residual solvent notes on clothes, bathroom accessories such as paper towels, bathroom tissues, sanitary napkins, towellets, disposable wash cloths, disposable diapers, and diaper pail deodorants, cleansers such as disinfectants and toilet bowl cleaners, cosmetic products such as antiperspirant and deodorants, general body deodorants in the form of powders, aerosols, liquids or solid, or hair care products such as hair sprays, conditioners, rinses, hair colors and dyes, permanent waves, depilatories, hair straighteners, hair groom applications such as pomade, creams and lotions, medicated hair care products containing such ingredients as selenium sulphide, coal tar or salicylates, or shampoos, or foot care products such as foot powders, liquids or colognes, after shaves and body lotions, or soaps and synthetic detergents such as bars, liquids, foams or powders, odor control such as during manufacturing processes, such as in the textile finishing industry and the printing industry (inks and paper), effluent control such as in processes involved in pulping, stock yard and meat processings, sewage treatment, garbage bags, or garbage disposal, or in product odor control as in textile finished goods, rubber finished goods or car fresheners, agricultural and pet care products such as dog and hen house effluents and domestic animal and pet care products such as deodorants, shampoo or cleaning agents, or animal litter material and in large scale closed air systems such as auditoria, and subways and transport systems.

Thus, it will be seen that the composition of the invention is usually one in which the malodor counteractant is present together with a carrier by means of which or from which the malodor counteractant can be introduced into air space wherein the malodor is present, or a substrate on which the malodor has deposited. For example, the carrier can be an aerosol propellant such as a chlorofluoro-methane, or a solid such as a wax, plastics material, rubber, inert powder or gel. In a wick-type air freshener, the carrier is a substantially odorless liquid of low volatility. In several applications, a composition of the invention contains a surface active agent or a disinfectant, while in others, the malodor counteractant is present on a fibrous substrate. In many compositions of the invention there is also present a fragrance component which imparts a fragrance to the composition. The fragrances stated above can all be employed.

Malodor counteracting effective amount is understood to mean the amount of the inventive malodor counteractant employed in a functional product that is organoleptically effective to abate a given malodor while reducing the combined intensity of the odor level, wherein the given malodor is present in air space or has deposited on a substrate. The exact amount of malodor counteractant agent employed may vary depending upon the type of malodor counteractant, the type of the carrier employed, and the level of malodor counteractancy desired. In general, the amount of malodor counteractant agent present is the ordinary dosage required to obtain the desired result. Such dosage is known to the skilled practitioner in the art. In a preferred embodiment, when used in conjunction with malodorous solid or liquid functional products, e.g., soap and detergent, the compounds of the present invention may be present in an amount ranging from about 0.005 to about 50 weight percent, preferably from about 0.01 to about 20 weight percent, and more preferably from about 0.05 to about 5 weight percent, and when used in conjunction with malodorous gaseous functional products, the compounds of the present invention may be present in an amount ranging from about 0.1 to 10 mg per cubic meter of air.

The following are provided as specific embodiments of the present invention. Other modifications of this invention will be readily apparent to those skilled in the art. Such modifications are understood to be within the scope of this invention. As used herein all percentages are weight percent unless otherwise noted, ppm is understood to stand for parts per million, L is understood to be liter, mL is understood to be milliliter, g is understood to be gram, Kg is understood to be kilogram, mol is understood to be mole, mmol is understood to be millimole, psi is understood to be pound-force per square inch, and mmHg be millimeters (mm) of mercury (Hg). IFF as used in the examples is understood to mean International Flavors & Fragrances Inc., New York, N.Y., USA.

EXAMPLE I

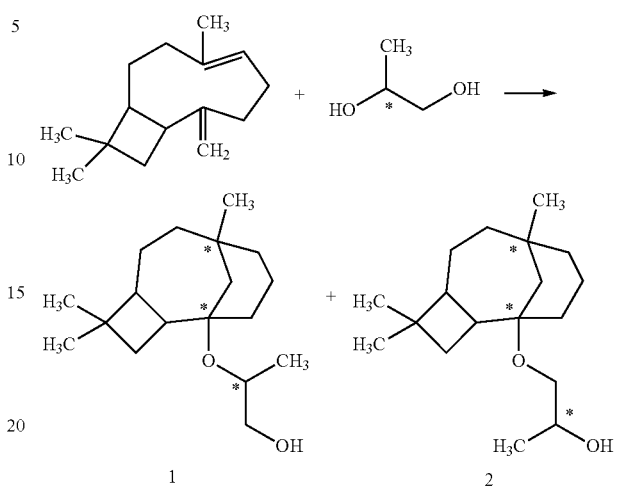

Preparation of 2-((4,4,8-Trimethyltricyclo[6.3.1.0$^{2,5}$]dodecan-1-yl)oxy)propan-1-ol (Structure 1) and 1-((4,4,8-Trimethyltricyclo[6.3.1.0$^{2,5}$]dodecan-1-yl)oxy)propan-2-ol (Structure 2): Caryophyllene (500 g, 2.4 mol) and propane-1,2-diol (292 g, 3.8 mol) were charged into a reactor. Phosphoric acid (8.29 g, 85% purity) was added. The reaction mixture was heated to 125° C. for 8-16 hours. The progress and completion of the reaction were monitored by gas-liquid chromatograph (GLC). The reaction was then cooled to 80° C., diluted with ethyl acetate (100 mL) and washed with sodium bicarbonate to quench phosphoric acid. The organic layer was separated, washed with brine, distilled and rushed over to provide the crude product (463 g). The crude product was further fractionated to provide a positional isomeric mixture containing major products 2-((4,4,8-trimethyltricyclo[6.3.1.0$^{2,5}$]dodecan-1-yl)oxy)propan-1-ol (Structure 1) (~23%) and 1-((4,4,8-trimethyltricyclo[6.3.1.0$^{2,5}$]dodecan-1-yl)oxy)propan-2-ol (Structure 2) (~60%), and minor products 2(or 1)-((1,4,4-trimethyltricyclo[6.3.1.0$^{2,5}$]dodecan-8-yl)oxy)propan-1(or 2)-ol (~10%) and 2(or 1)-((1,1,7-trimethyldecahydro-3a,7-methanocyclopenta[8]annulen-3-yl)oxy)propan-1(or 2)-ol (~7%). The mixture had a boiling point of 140° C. at 1.0 mmHg Each of the isomers (where * denotes a chiral center) might further contain stereoisomers including (2R)-2-(or 1)-(((1S,8S)—, (2R)-2-(or 1)-(((1S,8R)—, (2R)-2-(or 1)-(((1R,8R)—, (2R)-2(or 1)-(((1R,8S)—, (2S)-2-(or 1)-(((1S,8S)—, (2S)-2(or 1)-(((1S,8R)—, (2S)-2-(or 1)-(((1R,8R)—, and (2S)-2(or 1)-(((1R,8S)-4,4,8-trimethyltricyclo[6.3.1.0$^{2,5}$]dodec anyl)oxy)propanol. $^1$H NMR (500 MHz, CDCl$_3$) δ: 3.67-3.95 (m, 1H), 2.97-3.37 (m, 2H), 2.05-2.29 (m, 1H), 1.17-1.90 (m, 12H), 0.99-1.17 (m, 6H), 0.98 (s, 3H), 0.97 (s, 3H), 0.87 (s, 3H).

The obtained mixture as well as each isomer was described as having amber, wood, cedar and dry notes. Among all the isomers, Structure 1 exhibited particularly strong and long-lasting notes.

EXAMPLE II

Preparation of (2R)-2-((4,4,8-Trimethyltricyclo[6.3.1.0$^{2,5}$]dodecan-1-yl)oxy)propan-1-ol (Structure 1a) and (2R)-1-((4,4,8-Trimethyltricyclo[6.3.1.0$^{2,5}$]dodecan-1-yl)

oxy)propan-2-ol (Structure 2a): An isomeric mixture similarly prepared according to EXAMPLE I with (R)-propane-1,2-diol contained major products (2R)-2-((4,4,8-trimethyltricyclo[6.3.1.0$^{2,5}$]dodecan-1-yl)oxy)propan-1-ol (Structure 1a) (~22%) and (2R)-1-((4,4,8-trimethyltricyclo[6.3.1.0$^{2,5}$]dodecan-1-yl)oxy)propan-2-ol (Structure 2) (~60%), and minor products (2R)-2-(or 1)-((1,4,4-trimethyltricyclo[6.3.1.0$^{2,5}$]dodecan-8-yl)oxy)propan-1(or 2)-ol (~3%), (2R)-2-((1,1,7-trimethyldecahydro-3a,7-methanocyclopenta[8]annulen-3-yl)oxy)propan-1-ol (~8%) and (2R)-1-((1,1,7-trimethyldecahydro-3a,7-methanocyclopenta[8]annulen-3-yl)oxy)propan-2-ol (~7%).

(2R)-2-((4,4,8-Trimethyltricyclo[6.3.1.0$^{2,5}$]dodecan-1-yl)oxy)propan-1-ol (Structure 1a) had the following NMR spectral characteristics:

$^1$H NMR (500 MHz, CDCl$_3$) δ: 3.73-3.80 (m, 1H), 3.47-3.54 (m, 1H), 3.33-3.39 (m, 1H), 2.18-2.30 (m, 1H), 2.07-2.14 (m, 1H), 1.61-1.82 (m, 4H), 1.21-1.60 (m, 8H), 1.18 (d, J=12.9 Hz, 1H), 1.00-1.16 (m, 5H), 0.99 (s, 3H), 0.98 (s, 3H), 0.88 (s, 3H).

(2R)-1-((4,4,8-Trimethyltricyclo[6.3.1.0$^{2,5}$]dodecan-1-yl)oxy)propan-2-ol (Structure 2a) had the following NMR spectral characteristics:

$^1$H NMR (400 MHz, CDCl$_3$) δ: 3.83-4.00 (m, 1H), 3.11-3.29 (m, 2H), 2.45-2.65 (br s, 1H), 2.10-2.33 (m, 2H), 1.21-1.95 (m, 11H), 0.95-1.20 (m, 12H), 0.90 (s, 3H).

The obtained mixture was described as having amber, wood and sawdust-like notes. Among all the isomers, Structure 1a exhibited the strongest and longest-lasting notes.

EXAMPLE III

Preparation of (2S)-2-((4,4,8-Trimethyltricyclo[6.3.1.0$^{2,5}$]dodecan-1-yl)oxy)propan-1-ol (Structure 1b) and (2S)-1-((4,4,8-Trimethyltricyclo[6.3.1.0$^{2,5}$]dodecan-1-yl)oxy)propan-2-ol (Structure 2b): An isomeric mixture similarly prepared according to EXAMPLE I with (S)-propane-1,2-diol contained products (2S)-2-((4,4,8-trimethyltricyclo[6.3.1.0$^{2,5}$]dodecan-1-yl)oxy)propan-1-ol (Structure 1b) (~6%), (2S)-1-((4,4,8-trimethyltricyclo[6.3.1.0$^{2,5}$]dodecan-1-yl)oxy)propan-2-ol (Structure 2b) (~80%), (2S)-2(or 1)-((1,4,4-trimethyltricyclo[6.3.1.0$^{2,5}$]dodecan-8-yl)oxy)propan-1(or 2)-ol (trace amounts) and (2S)-2(or 1)-((1,1,7-trimethyldecahydro-3a,7-methanocyclopenta[8]annulen-3-yl)oxy)propan-1(or 2)-ol (~14%).

(2S)-2-((4,4,8-Trimethyltricyclo[6.3.1.0$^{2,5}$]dodecan-1-yl)oxy)propan-1-ol (Structure 1b) had the following NMR spectral characteristics:

$^1$H NMR (500 MHz, CDCl$_3$) δ3.70-3.82 (m, 1H), 3.42-3.50 (m, 1H), 3.27-3.35 (m, 1H), 2.18-2.31 (m, 1H), 1.99-2.11 (m, 1H), 1.78-1.87 (m, 1H), 1.60-1.78 (m, 4H), 1.28-1.59 (m, 7H), 1.06-1.16 (m, 5H), 1.00-1.08 (m, 1H), 0.99 (s, 3H), 0.98 (s, 3H), 0.89 (s, 3H).

(2S)-1-((4,4,8-Trimethyltricyclo[6.3.1.0$^{2,5}$]dodecan-1-yl)oxy)propan-2-ol (Structure 2b) had the following NMR spectral characteristics:

$^1$H NMR (400 MHz, CDCl$_3$) δ: 3.80-3.99 (m, 1H), 3.38 (dd, J=9.0, 3.3 Hz, 1H), 3.08 (dd, J=9.0, 8.7 Hz, 1H), 2.60 (br s, 1H), 2.14-2.27 (m, 1H), 1.78-1.93 (m, 1H), 1.67-1.78 (m, 3H), 1.18-1.67 (m, 8H), 1.02-1.18 (m, 6H), 1.01 (s, 3H), 1.00 (s, 3H), 0.90 (s, 3H).

The obtained mixture was described as having wood note. Among all the isomers, Structure 1b exhibited the strongest and longest-lasting notes.

EXAMPLE IV

Preparation of 2-((4,4,8-Trimethyltricyclo[6.3.1.0$^{2,5}$]dodecan-1-yl)oxy)butan-1-ol (Structure 3) and 1-((4,4,8-Trimethyltricyclo[6.3.1.0$^{2,5}$]dodecan-1-yl)oxy)butan-2-ol (Structure 4): An isomeric mixture similarly prepared according to EXAMPLE I with butane-1,2-diol contained major products 2-((4,4,8-trimethyltricyclo[6.3.1.0$^{2,5}$]dodecan-1-yl)oxy)butan-1-ol (Structure 3) (~20%) and 1-((4,4,8-trimethyltricyclo[6.3.1.0$^{2,5}$]dodecan-1-yl)oxy)butan-2-ol (Structure 4) (~50%), and minor products 2(or 1)-((1,4,4-trimethyltricyclo[6.3.1.0$^{2,5}$]dodecan-8-yl)oxy)butan-1 (or 2)-ol (~18%) and 2(or 1)-((1,1,7-trimethyldecahydro-3a,7-methanocyclopenta[8]annulen-3-yl)oxy)butan-1(or 2)-ol (~12%).

2-((4,4,8-Trimethyltricyclo[6.3.1.0$^{2,5}$]dodecan-1-yl)oxy)butan-1-ol (Structure 3) had the following NMR spectral characteristics:

$^1$H NMR (500 MHz, CDCl$_3$) δ: 3.50-3.58 (m, 1H), 3.00-3.45 (m, 2H), 1.94-2.31 (m, 1H), 1.19-1.88 (m, 14H), 1.00-1.17 (m, 3H), 0.92-1.00 (m, 9H), 0.88 (s, 3H).

1-((4,4,8-Trimethyltricyclo[6.3.1.0$^{2,5}$]dodecan-1-yl)oxy)butan-2-ol (Structure 4) had the following NMR spectral characteristics:

$^1$H NMR (500 MHz, CDCl$_3$) δ: 3.58-3.71 (m, 1H), 3.00-3.45 (m, 2H), 1.94-2.31 (m, 1H), 1.19-1.88 (m, 14H), 1.00-1.17 (m, 3H), 0.92-1.00 (m, 9H), 0.88 (s, 3H).

The obtained mixture was described as having strong amber, wood, cedar and dry notes. Among all the isomers, Structure 3 exhibited particularly strong and long-lasting notes.

EXAMPLE V

Preparation of 2-((4,4,8-Trimethyltricyclo[6.3.1.0$^{2,5}$]dodecan-1-yl)oxy)pentan-1-ol (Structure 5) and 1-((4,4,8-Trimethyltricyclo[6.3.1.0$^{2,5}$]dodecan-1-yl)oxy)pentan-2-ol (Structure 6): An isomeric mixture similarly prepared according to EXAMPLE I with pentane-1,2-diol contained major products 2-((4,4,8-trimethyltricyclo[6.3.1.0$^{2,5}$]dodecan-1-yl)oxy)pentan-1-ol (Structure 5) (~20%) and 1-((4,4,8-trimethyltricyclo[6.3.1.0$^{2,5}$]dodecan-1-yl)oxy)pentan-2-ol (Structure 6) (~52%), and minor products 2(or 1)-((1,4,4-trimethyltricyclo[6.3.1.0$^{2,5}$]dodecan-8-yl)oxy)pentan-1(or 2)-ol (~22%) and 2(or 1)-((1,1,7-trimethyldecahydro-3a,7-methanocyclopenta[8]annulen-3-yl)oxy)pentan-1(or 2)-ol (~6%).

2-((4,4,8-Trimethyltricyclo[6.3.1.0$^{2,5}$]dodecan-1-yl)oxy)pentan-1-ol (Structure 5) had the following NMR spectral characteristics:

$^1$H NMR (400 MHz, CDCl$_3$) δ: 3.53-3.86 (m, 1H), 2.96-3.48 (m, 2H), 2.35-2.66 (m, 1H), 1.95-2.32 (m, 1H), 1.19-1.93 (m, 17H), 0.60-1.18 (m, 14H).

1-((4,4,8-Trimethyltricyclo[6.3.1.0$^{2,5}$]dodecan-1-yl)oxy)pentan-2-ol (Structure 6) had the following NMR spectral characteristics:

$^1$H NMR (400 MHz, CDCl$_3$) δ: 3.53-3.86 (m, 1H), 2.96-3.48 (m, 2H), 2.35-2.66 (m, 1H), 1.95-2.32 (m, 1H), 1.19-1.93 (m, 17H), 0.60-1.18 (m, 14H).

The obtained mixture was described as having strong amber, wood, cedar and dry notes. Among all the isomers, Structure 5 exhibited particularly strong and long-lasting notes.

EXAMPLE VI

Preparation of (2R)-2-((4,4,8-Trimethyltricyclo[6.3.1.0$^{2,5}$]dodecan-1-yl)oxy)pentan-1-ol (Structure 5a) and (2R)-1-((4,4,8-Trimethyltricyclo[6.3.1.0$^{2,5}$]dodecan-1-yl)oxy)pentan-2-ol (Structure 6a): (R)-pentane-1,2-diol was first prepared according to Shaus et al. (Journal of the American Chemical Society (2002) 124: 1307-1315). An isomeric mixture was then similarly prepared according to EXAMPLE I with (R)-pentane-1,2-diol containing major products (2R)-2-((4,4,8-trimethyltricyclo[6.3.1.0$^{2,5}$]dodecan-1-yl)oxy)pentan-1-ol (Structure 5a) (~16%) and (2R)-1-((4,4,8-trimethyltricyclo[6.3.1.0$^{2,5}$]dodecan-1-yl)oxy)pentan-2-ol (Structure 6a) (~58%), and minor products (2R)-2-(or 1)-((1,4,4-trimethyltricyclo[6.3.1.0$^{2,5}$]dodecan-8-yl)oxy)pentan-1(or 2)-ol (~19%), (2R)-2-((1,1,7-trimethyldecahydro-3a,7-methanocyclopenta[8]annulen-3-yl)oxy)pentan-1-ol (~2%) and (2R)-1-((1,1,7-trimethyldecahydro-3a,7-methanocyclopenta[8]annulen-3-yl)oxy)pentan-2-ol (~5%).

(2R)-2-((4,4,8-Trimethyltricyclo[6.3.1.0$^{2,5}$]dodecan-1-yl)oxy)pentan-1-ol (Structure 5a) had the following NMR spectral characteristics:

$^1$H NMR (600 MHz, CDCl$_3$) δ: 3.56-3.64 (m, 2H), 3.39-3.50 (m, 1H), 2.22-2.34 (m, 1H), 2.10-2.20 (m, 1H), 1.74-1.87 (m, 2H), 1.62-1.74 (m, 2H), 1.24-1.61 (m, 12H), 1.20 (d, J=12.4 Hz, 1H), 1.10-1.17 (m, 1H), 1.02-1.08 (m, 1H), 1.01 (s, 3H), 1.0 (s, 3H), 0.91 (t, J=7.3 Hz, 3H), 0.90 (s, 3H).

(2R)-1-((4,4,8-Trimethyltricyclo[6.3.1.0$^{2,5}$]dodecan-1-yl)oxy)pentan-2-ol (Structure 6a) had the following NMR spectral characteristics:

$^1$H NMR (600 MHz, CDCl$_3$) δ: 3.70-3.79 (m, 1H), 3.27 (dd, J=9.0, 3.1 Hz, 1H), 3.21 (dd, J=9.0, 8.3 Hz, 1H), 2.52 (s, 1H), 2.11-2.26 (m, 1H), 1.79-1.90 (m, 1H), 1.60-1.76 (m, 5H), 1.28-1.59 (m, 10H), 1.11-1.19 (m, 2H), 1.03-1.10 (m, 2H), 1.01 (s, 3H), 1.00 (s, 3H), 0.95 (t, J=7.2 Hz, 3H), 0.90 (s, 3H).

(2R)-2(or 1)-((1,4,4-Trimethyltricyclo[6.3.1.0$^{2,5}$]dodecan-8-yl)oxy)pentan-1(or 2)-ol had the following NMR spectral characteristics:

$^1$H NMR (600 MHz, CDCl$_3$) δ: 3.62-3.73 (m, 1H), 3.40 (dd, J=8.8, 3.1 Hz, 1H), 3.21 (dd, 8.8, 8.6 Hz, 1H), 2.50 (br s, 1H), 2.00-2.09 (m, 1H), 1.79-1.85 (m, 1H), 1.72-1.78 (m 2H), 1.65-1.71 (m, 3H), 1.56-1.65 (m, 2H), 1.44-1.55 (m, 3H), 1.29-1.44 (m, 6H), 1.07-1.13 (m, 1H), 1.04 (d, J=12.8 Hz, 1H), 1.00 (s, 3H), 0.99 (s, 3H), 0.95 (t, J=7.1 Hz, 3H), 0.83 (3H).

(2R)-2-((1,1,7-Trimethyldecahydro-3a,7-methanocyclopenta[8]annulen-3-yl)oxy)pentan-1-ol had the following NMR spectral characteristics:

$^1$H NMR (600 MHz, CDCl$_3$) δ: 3.64-3.76 (m, 1H), 3.50 (dd, J=9.8. 5.6 Hz, 1H), 3.44-3.48 (m, 1H), 3.38-3.43 (m, 1H), 1.67 (dd, J=11.9, 5.6 Hz, 1H), 1.14-1.64 (m, 16H), 1.06 (s, 3H), 0.98-1.03 (m, 2H), 0.94 (t, J=7.2 Hz, 3H), 0.90 (s, 3H), 0.87 (s, 3H).

(2R)-1-((1,1,7-Trimethyldecahydro-3a,7-methanocyclopenta[8]annulen-3-yl)oxy)pentan-2-ol had the following NMR spectral characteristics:

$^1$H NMR (600 MHz, CDCl$_3$) δ: 3.75-3.82 (m, 1H), 3.51 (dd, J=9.3, 3.1 Hz, 1H), 3.41 (dd, J=9.3, 5.5 Hz, 1H), 3.24 (dd, J=9.3, 8.0 Hz, 1H), 1.12-1.78 (m, 14H), 0.99-1.10 (m, 8H), 0.96 (t, J=6.9 Hz, 3H), 0.90 (s, 3H), 0.88 (s, 3H).

The obtained mixture was described as having very strong amber, wood, cedar and dry notes. Among all the isomers, Structure 5a exhibited particularly strong and long-lasting notes.

EXAMPLE VII

Preparation of (2S)-2-((4,4,8-Trimethyltricyclo[6.3.1.0$^{2,5}$]dodecan-1-yl)oxy)pentan-1-ol (Structure 5b) and (2S)-1-((4,4,8-Trimethyltricyclo[6.3.1.0$^{2,5}$]dodecan-1-yl)oxy)pentan-2-ol (Structure 6b): (S)-pentane-1,2-diol was first prepared according to Shaus et al. (Journal of the American Chemical Society (2002) 124: 1307-1315). An isomeric mixture was then similarly prepared according to EXAMPLE I with (S)-pentane-1,2-diol containing major products (2S)-2-((4,4,8-trimethyltricyclo[6.3.1.0$^{2,5}$]dodecan-1-yl)oxy)pentan-1-ol (Structure 5b) (~17%) and (2S)-1-((4,4,8-trimethyltricyclo[6.3.1.0$^{2,5}$]dodecan-1-yl)oxy)pentan-2-ol (Structure 6b) (~56%), and minor products (2S)-2(or 1)-((1,4,4-trimethyltricyclo[6.3.1.0$^{2,5}$]dodecan-8-yl)oxy)pentan-1(or 2)-ol (~20%), (2S)-2-((1,1,7-trimethyldecahydro-3a,7-methanocyclopenta[8]annulen-3-yl)oxy)pentan-1-ol (<2%) and (2S)-1-((1,1,7-trimethyldecahydro-3a,7-methanocyclopenta[8]annulen-3-yl)oxy)pentan-2-ol (~5%).

(2S)-2-((4,4,8-Trimethyltricyclo[6.3.1.0$^{2,5}$]dodecan-1-yl)oxy)pentan-1-ol (Structure 5b) had the following NMR spectral characteristics:

$^1$H NMR (600 MHz, CDCl$_3$) δ: 3.60-3.67 (m, 1H), 3.51-3.57 (m, 1H), 3.36-3.44 (m, 1H), 2.21-2.33 (m, 1H), 2.03 (br s, 1H), 1.83-1.89 (m, 1H), 1.75-1.82 (m, 1H), 1.66-1.75 (m, 2H), 1.61-1.66 (m, 1H), 1.45-1.60 (m, 6H), 1.30-1.44 (m, 5H), 1.10-1.20 (m, 2H), 1.02-1.07 (m, 1H), 1.01 (s, 3H), 1.00 (s, 3H), 0.96 (t, J=7.3 Hz, 3H), 0.92 (s, 3H).

(2S)-1-((4,4,8-Trimethyltricyclo[6.3.1.0$^{2,5}$]dodecan-1-yl)oxy)pentan-2-ol (Structure 6b) had the following NMR spectral characteristics:

$^1$H NMR (600 MHz, CDCl$_3$) δ: 3.68-3.78 (m, 1H), 3.41 (dd, J=9.0, 3.2 Hz, 1H), 3.11 (dd, J=9.0, 9.0 Hz, 1H), 2.15-2.24 (m, 1H), 1.81-1.88 (m, 1H), 1.68-1.79 (m, 3H), 1.60-1.67 (m, 2H), 1.26-1.56 (m, 10H), 1.13-1.18 (m, 1H), 1.12 (d, J=12.8 Hz, 1H), 1.04-1.10 (m, 1H), 1.01 (s, 3H), 1.00 (s, 3H), 0.95 (t, J=7.1 Hz, 3H), 0.91 (s, 3H).

(2S)-2 (or 1)-((1,4,4-Trimethyltricyclo[6.3.1.0$^{2,5}$]dodecan-8-yl)oxy)pentan-1(or 2)-ol had the following NMR spectral characteristics:

$^1$H NMR (600 MHz, CDCl$_3$) δ: 3.63-3.71 (m, 1H), 3.43 (dd, J=8.8, 3.1 Hz, 1H), 3.18 (dd, J=8.8, 8.2 Hz, 1H), 2.47 (br s, 1H), 1.97-2.08 (m, 1H), 1.58-1.80 (m, 8H), 1.24-1.54 (m, 9H), 1.04-1.14 (m, 2H), 1.00 (s, 3H), 0.99 (s, 3H), 0.95 (t, J=7.1 Hz, 3H), 0.83 (s, 3H).

(2S)-1-((1,1,7-trimethyldecahydro-3a,7-methanocyclopenta[8]annulen-3-yl)oxy)pentan-2-ol had the following NMR spectral characteristics:

$^1$H NMR (600 MHz, CDCl$_3$) δ: 3.73-3.80 (m, 1H), 3.46 (dd, J=9.3, 3.1 Hz, 1H), 3.42 (dd, J=9.3, 5.5 Hz, 1H), 3.28 (dd, J=9.3, 7.9 Hz, 1H), 2.39 (br s, 1H), 1.71 (dd, J=12.2, 5.5 Hz, 1H), 1.17-1.67 (m, 16H), 1.05 (s, 3H), 0.99-1.05 (m, 2H), 0.96 (t, J=7.1 Hz, 3H), 0.90 (s, 3H), 0.87 (s, 3H).

The obtained mixture was described as having strong amber, wood, slightly smoky and guaiac notes. Among all the isomers, Structure 5b exhibited the strongest and longest-lasting notes.

EXAMPLE VIII

Preparation of 2-((4,4,8-Trimethyltricyclo[6.3.1.0$^{2,5}$]dodecan-1-yl)oxy)hexan-1-ol (Structure 7) and 1-((4,4,8-Trimethyltricyclo[6.3.1.0$^{2,5}$]dodecan-1-yl)oxy)hexan-2-ol (Structure 8): An isomeric mixture similarly prepared according to EXAMPLE I with hexane-1,2-diol contained major products 2-((4,4,8-trimethyltricyclo[6.3.1.0$^{2,5}$]dodecan-1-yl)oxy)hexan-1-ol (Structure 7) (~21%) and 1-((4,4,8-trimethyltricyclo[6.3.1.0$^{2,5}$]dodecan-1-yl)oxy)hexan-2-ol (Structure 8) (~45%), and minor products 2(or 1)-((1,4,4-trimethyltricyclo[6.3.1.0$^{2,5}$]dodecan-8-yl)oxy)hexan-1(or 2)-ol (~28%) and 2(or 1)-((1,1,7-trimethyldecahydro-3a,7-methanocyclopenta[8]annulen-3-yl)oxy)hexan-1(or 2)-ol (~6%).

$^1$H NMR (500 MHz, CDCl$_3$) δ: 3.53-3.78 (m, 1H), 3.00-3.45 (m, 2H), 2.37-2.63 (m, 1H), 1.93-2.32 (m, 1H), 1.17-1.90 (m, 18H), 0.61-1.16 (m, 15H).

The obtained mixture was described as having amber and wood notes.

EXAMPLE IX

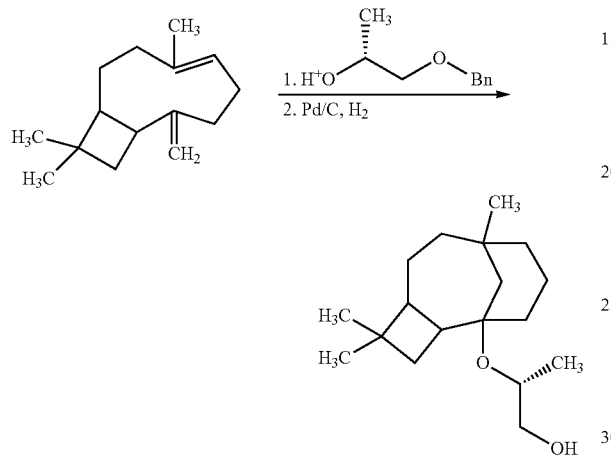

Preparation of (2R)-2-((4,4,8-Trimethyltricyclo[6.3.1.0$^{2,5}$]dodecan-1-yl)oxy)propan-1-ol (Structure 1a): Caryophyllene (2 g, 9.4 mmol) and (R)-1-(Benzyloxy)propan-2-ol (1.3 g, 7.8 mol) were charged into a reactor. Phosphoric acid (40 mg, 85% purity) was added. The reaction mixture was heated to 125° C. for 8 hours. The progress and completion of the reaction were monitored by GLC. The reaction was then cooled to 80° C., diluted with ethyl acetate (10 mL) and washed with sodium bicarbonate. The organic layer was separated, washed with brine and concentrated to provide a first crude product, which was purified by silica gel chromatography using a gradient of hexanes and ethyl acetate. The isolated benzylated product was hydrogenated using 5% palladium on carbon (Pd/C) at 30° C. and hydrogen (100 psi) to provide a second crude product, which was concentrated and then purified by silica gel chromatography using a gradient of hexanes and ethyl acetate to afford the product (2R)-2-((4,4,8-trimethyltricyclo[6.3.1.0$^{2,5}$]dodecan-1-yl)oxy)propan-1-ol (Structure 1a) (~99%).

$^1$H NMR (500 MHz, CDCl$_3$) δ: 3.73-3.80 (m, 1H), 3.47-3.54 (m, 1H), 3.33-3.39 (m, 1H), 2.18-2.30 (m, 1H), 2.07-2.14 (m, 1H), 1.61-1.82 (m, 4H), 1.21-1.60 (m, 8H), 1.18 (d, J=12.9 Hz, 1H), 1.00-1.16 (m, 5H), 0.99 (s, 3H), 0.98 (s, 3H), 0.88 (s, 3H)

(2R)-2-((4,4,8-Trimethyltricyclo[6.3.1.0$^{2,5}$]dodecan-1-yl)oxy)propan-1-ol was described as having strong amber, dry wood and cedar notes.

EXAMPLE X

Preparation of (2S)-2-((4,4,8-Trimethyltricyclo[6.3.1.0$^{2,5}$]dodecan-1-yl)oxy)propan-1-ol (Structure 1b): (2S)-2-((4,4,8-Trimethyltricyclo[6.3.1.0$^{2,5}$]dodecan-1-yl)oxy)propan-1-ol (Structure 1b) (~99%) was similarly prepared according to EXAMPLE IX with (S)-1-(benzyloxy)propan-2-ol.

$^1$H NMR (500 MHz, CDCl$_3$) δ: 3.70-3.82 (m, 1H), 3.42-3.50 (m, 1H), 3.27-3.35 (m, 1H), 2.18-2.31 (m, 1H), 1.99-2.11 (m, 1H), 1.78-1.87 (m, 1H), 1.60-1.78 (m, 4H), 1.28-1.59 (m, 7H), 1.06-1.16 (m, 5H), 1.00-1.08 (m, 1H), 0.99 (s, 3H), 0.98 (s, 3H), 0.89 (s, 3H).

The obtained (2S)-2-((4,4,8-trimethyltricyclo[6.3.1.0$^{2,5}$]dodecan-1-yl)oxy)propan-1-ol was described as having fleeting amber note.

EXAMPLE XI

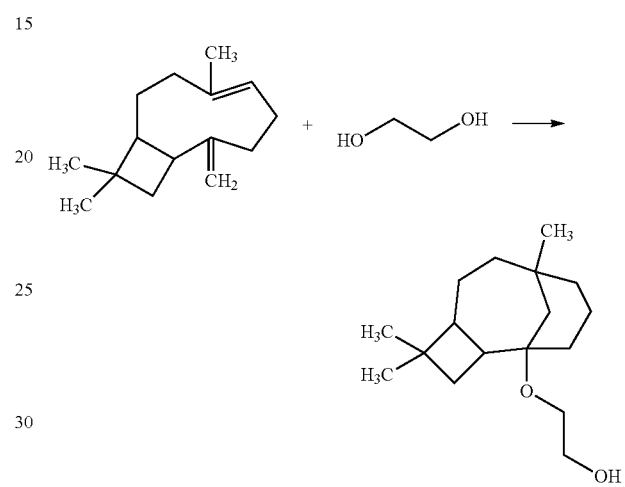

Preparation of 2-((4,4,8-Trimethyltricyclo[6.3.1.0$^{2,5}$]dodecan-1-yl)oxy)ethan-1-ol (Structure A): An isomeric mixture similarly prepared according to EXAMPLE I with ethylene glycol contained a major product 2-((4,4,8-trimethyltricyclo[6.3.1.0$^{2,5}$]dodecan-1-yl)oxy)ethan-1-ol (~80%) and a minor product 2-((1,1,7-trimethyldecahydro-3a,7-methanocyclopenta[8]annulen-3-yl)oxy)ethan-1-ol (~20%).

$^1$H NMR (400 MHz, CDCl$_3$) δ: 3.61-3.79 (m, 2H), 3.47-3.59 (m, 1H), 3.30-3.47 (m, 1H), 2.10-2.29 (m, 1H), 1.80-1.90 (m, 1H), 1.45-1.80 (m, 8H), 1.20-1.45 (m, 3H), 1.03-1.19 (m, 3H), 1.01 (s, 3H), 1.00 (s, 3H), 0.90 (s, 3H)

The obtained mixture was described as being odorless.

EXAMPLE XII

In addition, the following analogs were similarly prepared.

3-((4,4,8-Trimethyltricyclo[6.3.1.0$^{2,5}$]dodecan-1-yl)oxy)butan-2-ol (Structure 9)

$^1$H NMR (400 MHz, CDCl$_3$) δ: 3.67-3.83 (m, 1H), 3.55-3.66 (m, 1H), 2.16-2.30 (m, 1H), 1.02-1.90 (m, 21H), 1.01 (s, 3H), 1.00 (s, 3H), 0.88-0.92 (m, 3H).

3-((4,4,8-Trimethyltricyclo[6.3.1.0$^{2,5}$]dodecan-1-yl)oxy)propan-1-ol (Structure B)

$^1$H NMR (400 MHz, CDCl$_3$) δ: 3.71-3.86 (m, 2H), 3.57-3.70 (m, 1H), 3.43-3.54 (m, 1H), 2.10-2.25 (m, 1H), 1.03-1.90 (m, 17H), 1.01 (s, 3H), 1.00 (s, 3H), 0.89 (s, 3H).

4-((4,4,8-Trimethyltricyclo[6.3.1.0$^{2,5}$]dodecan-1-yl)oxy)butan-2-ol (Structure C)

$^1$H NMR (400 MHz, CDCl$_3$) δ: 3.92-4.10 (m, 1H), 3.37-3.92 (m, 2H), 2.12-2.42 (m, 1H), 1.03-1.91 (m, 20H), 0.94-1.01 (m, 6H), 0.85-0.93 (m, 3H).

2-Methyl-3-((4,4,8-trimethyltricyclo[6.3.1.0$^{2,5}$]dodecan-1-yl)oxy)propan-1-ol (Structure D)

$^1$H NMR (400 MHz, CDCl$_3$) δ: 3.18-3.72 (m, 4H), 2.11-2.27 (m, 1H), 1.91-2.09 (m, 1H), 1.02-1.89 (m, 15H), 0.95-1.02 (m, 6H), 0.88 (s, 3H), 0.78-0.86 (m, 3H).

2,2-Dimethyl-3-((4,4,8-trimethyltricyclo[6.3.1.0$^{2,5}$]dodecan-1-yl)oxy)propan-1-ol (Structure E)

$^1$H NMR (400 MHz, CDCl$_3$) δ: 3.13-3.59 (m, 4H), 1.96-2.26 (m, 1H), 1.02-1.92 (m, 15H), 0.79-1.01 (m, 15H).

(1-(((4,4,8-Trimethyltricyclo[6.3.1.0$^{2,5}$]dodecan-1-yl)oxy)methyl)cyclopropyl)methanol (Structure F)

$^1$H NMR (500 MHz, CDCl$_3$) δ: 3.19-3.61 (m, 4H), 2.10-2.21 (m, 1H), 1.78-1.88 (m, 1H), 1.02-1.77 (m, 14H), 1.00 (s, 3H), 0.98 (s, 3H), 0.88 (s, 3H), 0.39-0.57 (m, 4H).

N-(4,4,8-Trimethyltricyclo[6.3.1.0$^{2,5}$]dodecan-1-yl)acetamide (Structure G)

$^1$H NMR (400 MHz, CDCl$_3$) δ: 5.23-5.45 (br s, 1H), 2.25-2.40 (m, 2H), 1.91 (s, 3H), 1.65-1.83 (m, 4H), 1.29-1.65 (m, 6H), 1.17-1.29 (m, 2H), 1.25 (dd, J=10.3, 10.3 Hz, 1H), 1.20 (d, J=12.9 Hz, 1H), 0.97 (s, 3H), 0.96 (s, 3H), 0.86 (s, 3H).

EXAMPLE XIII

The fragrance properties of the above compounds were evaluated using (i) odor strength of 0 to 10, where 0=none, 1=very weak, 5=moderate, 10=extremely strong; and (ii) level of complexity, where 0=none, 1=very low, 5=moderate, 10=extremely high. Averaged scores are reported in the following:

| Compound | Odor Profile | Strength | Complexity |
|---|---|---|---|
| Structure 1/Structure 2 (EXAMPLE I) | Amber, wood, dry | 5 | 6 |
| Structure 1a/Structure 2a (EXAMPLE II) | Amber, wood, sawdust-like, dry | 7 | 6 |
| Structure 1b/Structure 2b (EXAMPLE III) | Wood | 4 | 3 |
| Structure 3/Structure 4 (EXAMPLE IV) | Amber, wood, cedar, dry | 9 | 7 |
| Structure 5/Structure 6 (EXAMPLE V) | Amber, wood, dry | 10 | 10 |
| Structure 5a/Structure 6a (EXAMPLE VI) | Amber, wood, cedar, dry | 10 | 8 |
| Structure 5b/Structure 6b (EXAMPLE VII) | Amber, wood, slight smoky guaiac-effect, dry | 7 | 8 |
| Structure 7/Structure 8 (EXAMPLE VIII) | Amber, wood, dry | 3 | 5 |
| Structure 1a (EXAMPLE IX) | Amber, wood, cedar, dry | 6 | 5 |
| Structure 1b (EXAMPLE X) | Amber, fleeting | 2 | 2 |
| Structure 9 | Fruity, intensity dropped quickly, amber note not detected | 7 | 5 |
| Structure A (EXAMPLE XI) | Odorless | 0 | 0 |
| Structure B | Odorless | 0 | 0 |
| Structure C | Odorless | 0 | 0 |
| Structure D | Guaiac, became odorless when dried | 2 | 2 |
| Structure E | Fruity, green, became odorless when dried | 3 | 3 |
| Structure F | Odorless | 0 | 0 |
| Structure G | Green, galbanum, moss, became odorless when dried | 4 | 2 |

EXAMPLE XIII (Continued)

As shown above, ((4,4,8-trimethyltricyclo[6.3.1.0$^{2,5}$]dodecan-1-yl)oxy) alcohols of Structures 1-9 and isomers thereof exhibited unique and highly desirable amber and wood notes, which were absent in Structures A-G. The odor profiles of Structure 5/Structure 6 are particularly strong and complex. Such advantageous properties are unexpected.

EXAMPLE XIV

The fragrance formula exemplified as follows demonstrates that 2-((4,4,8-trimethyltricyclo[6.3.1.0$^{2,5}$]dodecan-1-yl)oxy)pentan-1-ol (Structure 5) and 1-((4,4,8-trimethyltricyclo[6.3.1.0$^{2,5}$]dodecan-1-yl)oxy)pentan-2-ol (Structure 6) (obtained in EXAMPLE V) provided an initial rounding and richness to the odor. The accord became nicely enveloped, yielding a linear odor and volume over time with extended substantivity of floral notes.

| | Parts* | |
|---|---|---|
| Ingredients | − | + |
| BASIL OIL | 30.00 | 30.00 |
| BERGAMOT OIL CP BERGAPTFREE | 150.00 | 150.00 |
| COUMARIN | 30.00 | 30.00 |
| DIPROPYLENE GLYCOL | 87.00 | 37.00 |
| EUGENOL NAT EX CLOVE LEAF OIL | 30.00 | 30.00 |
| HEXADECANOLIDE | 350.00 | 350.00 |
| ISO BUTYL QUINOLINE | 3.00 | 3.00 |
| METHIONONE GAMMA A TOCO | 30.00 | 30.00 |
| STRUCTURE 5/STRUCTURE 6 | — | 50.00 |
| PATCHOULI OIL LIGHT BLO | 30.00 | 30.00 |
| VERTOFIX COEUR | 200.00 | 200.00 |
| VETIVER OIL HAITI | 60.00 | 60.00 |
| TOTAL | 1000.00 | 1000.00 |

*"+" represents a Structure 5/Structure 6 containing formula; and "−" represents a Structure 5/Structure 6 non-containing formula.

EXAMPLE XV

The fragrance formula exemplified as follows demonstrates that 2-((4,4,8-trimethyltricyclo[6.3.1.0$^{2,5}$]dodecan-1-yl)oxy)pentan-1-ol (Structure 5) and 1-((4,4,8-trimethyltricyclo[6.3.1.0$^{2,5}$]dodecan-1-yl)oxy)pentan-2-ol (Structure 6) (obtained in EXAMPLE V) imparted an overall brightening and increased volume to the top notes. The moss and wood notes were enhanced by the creation of an amber-wood character, providing attractive dry-down characters.

| | Parts* | |
|---|---|---|
| Ingredients | − | + |
| BACDANOL TOCO | 5.00 | 5.00 |
| BERGAMOT OIL CP BERGAPTFREE | 270.00 | 270.00 |
| DIPROPYLENE GLYCOL | 85.00 | 65.00 |
| MOSS-OAK ABS IFRA 43 LMR | 60.00 | 60.00 |
| STRUCTURE 5/STRUCTURE 6 | — | 20.00 |
| SYNTHETIC ROSE BASE | 360.00 | 360.00 |
| VERTOFIX COEUR | 200.00 | 200.00 |
| VETIVER OIL HAITI | 20.00 | 20.00 |
| TOTAL | 1000.00 | 1000.00 |

*"+" represents Structure 5/Structure 6 compound containing formula; and "−" represents a Structure 5/Structure 6 compound non-containing formula.

What is claimed is:

1. A compound having Formula I:

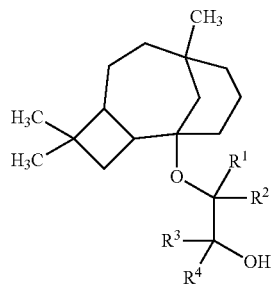

Formula I or an isomer thereof; wherein $R^1$, $R^2$, $R^3$ and $R^4$ are independently selected from the group consisting of hydrogen and a $C_{1-12}$ linear or branched alkyl group, with the proviso that $R^1$, $R^2$, $R^3$ and $R^4$ together contain 1-12 carbon atoms.

2. The compound of claim 1 having Formula II:

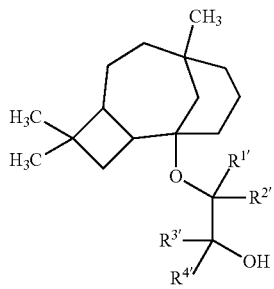

Formula II or an isomer thereof; wherein $R^{1\prime}$, $R^{2\prime}$, $R^{3\prime}$ and $R^{4\prime}$ are independently selected from the group consisting of hydrogen and a $C_{1-6}$ linear or branched alkyl group, with the proviso that $R^{1\prime}$, $R^{2\prime}$, $R^{3\prime}$ and $R^{4\prime}$ together contain 1-6 carbon atoms.

3. The compound of claim 2 selected from the group consisting of 2-((4,4,8-trimethyltricyclo[6.3.1.0$^{2,5}$]dodecan-1-yl)oxy) propan-1-ol;
1-((4,4,8-trimethyltricyclo[6.3.1.0$^{2,5}$]dodecan-1-yl)oxy) propan-2-ol;
2-((4,4,8-trimethyltricyclo[6.3.1.0$^{2,5}$]dodecan-1-yl)oxy) butan-1-ol;
1-((4,4,8-trimethyltricyclo[6.3.1.0$^{2,5}$]dodecan-1-yl)oxy) butan-2-ol;
2-((4,4,8-trimethyltricyclo[6.3.1.0$^{2,5}$]dodecan-1-yl)oxy) pentan-1-ol;
1-((4,4,8-trimethyltricyclo[6.3.1.0$^{2,5}$]dodecan-1-yl)oxy) pentan-2-ol;
2-((4,4,8-trimethyltricyclo[6.3.1.0$^{2,5}$]dodecan-1-yl)oxy) hexan-1-ol;
1-((4,4,8-trimethyltricyclo[6.3.1.0$^{2,5}$]dodecan-1-yl)oxy) hexan-2-ol;
3-((4,4,8-trimethyltricyclo[6.3.1.0$^{2,5}$]dodecan-1-yl)oxy) butan-2-ol;
an isomer thereof; and
a mixture thereof.

4. The compound of claim 3 is 2-((4,4,8-trimethyltricyclo [6.3.1.0$^{2,5}$]dodecan-1-yl)oxy)pentan-1-ol, 1-((4,4,8-trimethyltricyclo[6.3.1.0$^{2,5}$]dodecan-1-yl)oxy)pentan-2-ol, an isomer thereof or a mixture thereof.

5. A fragrance product containing the compound of claim 1.

6. The fragrance product of claim 5, wherein the fragrance product is selected from the group consisting of a perfume, a cologne, toilet water, a bar soap, a liquid soap, a shower gel, a foam bath, a cosmetic, a personal care product, a skin care product, a hair care product, a deodorant, an antiperspirant, a feminine care product, a baby care product, a family care product, a fabric product, an air care product, a fragrance delivery system, a cosmetic preparation, a cleaning product, a disinfectant, a washing agent, a dental and oral hygiene product, a health care and nutritional product and a food product.

7. A fragrance formulation comprising an olfactory acceptable amount of a compound having Formula I:

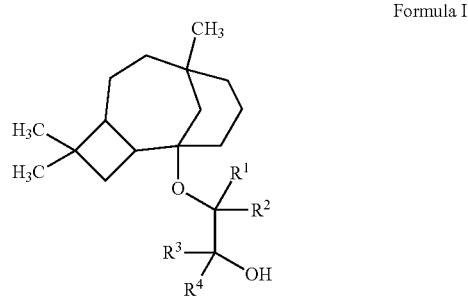

Formula I or an isomer thereof; wherein $R^1$, $R^2$, $R^3$ and $R^4$ are independently selected from the group consisting of hydrogen and a $C_{1-12}$ linear or branched alkyl group, with the proviso that $R^1$, $R^2$, $R^3$ and $R^4$ together contain 1-12 carbon atoms.

8. The fragrance formulation of claim 7, wherein the compound has Formula II:

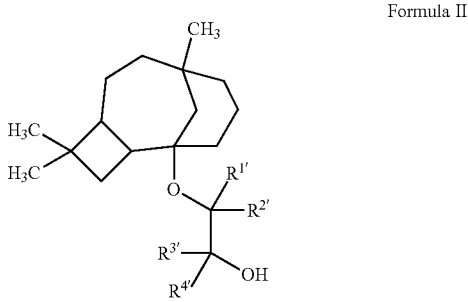

Formula II or an isomer thereof; wherein $R^{1\prime}$, $R^{2\prime}$, $R^{3\prime}$ and $R^{4\prime}$ are independently selected from the group consisting of hydrogen and a $C_{1-6}$ linear or branched alkyl group, with the proviso that $R^{1\prime}$, $R^{2\prime}$, $R^{3\prime}$ and $R^{4\prime}$ together contain 1-6 carbon atoms.

9. The fragrance formulation of claim 8, wherein the compound is selected from the group consisting of 2-((4,4,8-trimethyltricyclo[6.3.1.0$^{2,5}$]dodecan-1-yl)oxy) propan-1-ol;
1-((4,4,8-trimethyltricyclo[6.3.1.0$^{2,5}$]dodecan-1-yl)oxy) propan-2-ol;
2-((4,4,8-trimethyltricyclo[6.3.1.0$^{2,5}$]dodecan-1-yl)oxy) butan-1-ol;

1-((4,4,8-trimethyltricyclo[6.3.1.0$^{2,5}$]dodecan-1-yl)oxy) butan-2-ol;
2-((4,4,8-trimethyltricyclo[6.3.1.0$^{2,5}$]dodecan-1-yl)oxy) pentan-1-ol;
1-((4,4,8-trimethyltricyclo[6.3.1.0$^{2,5}$]dodecan-1-yl)oxy) pentan-2-ol;
2-((4,4,8-trimethyltricyclo[6.3.1.0$^{2,5}$]dodecan-1-yl)oxy) hexan-1-ol;
1-((4,4,8-trimethyltricyclo[6.3.1.0$^{2,5}$]dodecan-1-yl)oxy) hexan-2-ol;
3-((4,4,8-trimethyltricyclo[6.3.1.0$^{2,5}$]dodecan-1-yl)oxy) butan-2-ol;
an isomer thereof; and
a mixture thereof.

10. The fragrance formulation of claim 7, wherein the olfactory acceptable amount is from about 0.005 to about 50 weight percent of the fragrance formulation.

11. The fragrance formulation of claim 7, wherein the olfactory acceptable amount is from about 0.5 to about 25 weight percent of the fragrance formulation.

12. The fragrance formulation of claim 7, wherein the olfactory acceptable amount is from about 1 to about 10 weight percent of the fragrance formulation.

13. The fragrance formulation of claim 7 further comprising a polymer.

14. The fragrance formulation of claim 13, wherein the polymer is selected from the group consisting of polyacrylate, polyurea, polyurethane, polyacrylamide, polyester, polyether, polyamide, poly(acrylate-co-acrylamide), starch, silica, gelatin and gum Arabic, alginate, chitosan, polylactide, poly(melamine-formaldehyde), poly(urea-formaldehyde) and a combination thereof.

15. A method of improving, enhancing or modifying a fragrance formulation comprising the step of adding to the fragrance formulation an olfactory acceptable amount of a compound having Formula I:

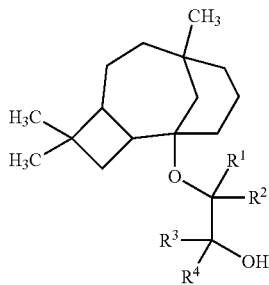

Formula I or an isomer thereof; wherein R$^1$, R$^2$, R$^3$ and R$^4$ are independently selected from the group consisting of hydrogen and a C$_{1-12}$ linear or branched alkyl group, with the proviso that R$^1$, R$^2$, R$^3$ and R$^4$ together contain 1-12 carbon atoms.

16. The method of claim 15, wherein the compound has Formula II:

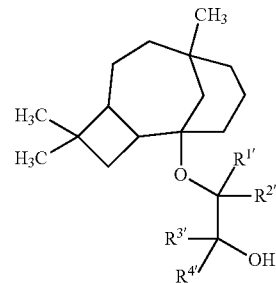

Formula II or an isomer thereof; wherein R$^{1'}$, R$^{2'}$, R$^{3'}$ and R$^{4'}$ are independently selected from the group consisting of hydrogen and a C$_{1-6}$ linear or branched alkyl group, with the proviso that R$^{1'}$, R$^{2'}$, R$^{3'}$ and R$^{4'}$ together contain 1-6 carbon atoms.

17. The method of claim 16, wherein the compound is selected from the group consisting of
2-((4,4,8-trimethyltricyclo[6.3.1.0$^{2,5}$]dodecan-1-yl)oxy) propan-1-ol;
1-((4,4,8-trimethyltricyclo[6.3.1.0$^{2,5}$]dodecan-1-yl)oxy) propan-2-ol;
2-((4,4,8-trimethyltricyclo[6.3.1.0$^{2,5}$]dodecan-1-yl)oxy) butan-1-ol;
1-((4,4,8-trimethyltricyclo[6.3.1.0$^{2,5}$]dodecan-1-yl)oxy) butan-2-ol;
2-((4,4,8-trimethyltricyclo[6.3.1.0$^{2,5}$]dodecan-1-yl)oxy) pentan-1-ol;
1-((4,4,8-trimethyltricyclo[6.3.1.0$^{2,5}$]dodecan-1-yl)oxy) pentan-2-ol;
2-((4,4,8-trimethyltricyclo[6.3.1.0$^{2,5}$]dodecan-1-yl)oxy) hexan-1-ol;
1-((4,4,8-trimethyltricyclo[6.3.1.0$^{2,5}$]dodecan-1-yl)oxy) hexan-2-ol;
3-((4,4,8-trimethyltricyclo[6.3.1.0$^{2,5}$]dodecan-1-yl)oxy) butan-2-ol;
an isomer thereof; and
a mixture thereof.

18. The method of claim 15, wherein the olfactory acceptable amount is from about 0.005 to about 50 weight percent of the fragrance formulation.

19. The method of claim 15, wherein the olfactory acceptable amount is from about 0.5 to about 25 weight percent of the fragrance formulation.

20. The method of claim 15, wherein the olfactory acceptable amount is from about 1 to about 10 weight percent of the fragrance formulation.

* * * * *